United States Patent
Bublewitz et al.

(10) Patent No.: US 10,307,343 B2
(45) Date of Patent: Jun. 4, 2019

(54) POLYMERIZABLE DENTAL MATERIAL WITH A PHASE TRANSFER CATALYST

(71) Applicant: Kettenbach GmbH & Co. KG, Eschenburg (DE)

(72) Inventors: Alexander Bublewitz, Herborn (DE); Alexander Theis, Eschenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 15/064,397

(22) Filed: Mar. 8, 2016

(65) Prior Publication Data

US 2016/0262987 A1  Sep. 15, 2016

(30) Foreign Application Priority Data

Mar. 9, 2015  (DE) .......... 10 2015 103 427

(51) Int. Cl.
*A61K 6/083* (2006.01)
*A61K 6/00* (2006.01)

(52) U.S. Cl.
CPC .............. *A61K 6/083* (2013.01); *A61K 6/005* (2013.01); *A61K 6/0047* (2013.01); *A61K 6/0052* (2013.01); *A61K 6/0055* (2013.01)

(58) Field of Classification Search
CPC ................................ A61K 6/005; A61K 6/083
See application file for complete search history.

(56) References Cited

U.S. PATENT DOCUMENTS

| | | | |
|---|---|---|---|
| 7,741,381 B2 | 6/2010 | Nakata et al. | |
| 2004/0192805 A1 | 9/2004 | Finger | |
| 2010/0267856 A1* | 10/2010 | Shinoda | A61K 6/083 522/11 |
| 2010/0292363 A1 | 11/2010 | Neffgen et al. | |
| 2012/0202913 A1 | 8/2012 | Kawana et al. | |
| 2015/0231041 A1 | 8/2015 | Bublewitz et al. | |

FOREIGN PATENT DOCUMENTS

| | | |
|---|---|---|
| EP | 1374445 A2 | 1/2004 |
| EP | 1444972 B1 | 3/2006 |
| EP | 1790323 A1 | 5/2007 |
| EP | 1780223 B1 | 7/2010 |
| EP | 2237763 B1 | 10/2010 |
| EP | 2409997 A1 | 1/2012 |
| EP | 2554154 A1 | 2/2013 |
| WO | 9522956 A1 | 8/1995 |
| WO | 02080487 A2 | 10/2002 |
| WO | 2014033280 A2 | 3/2014 |

OTHER PUBLICATIONS

Turovskii, N.A., Opeida, I.A., Kushch, O.V., Baranovskii, E. L. Russ. J. Appl. Chem. (2004) 77: 1869.*
Search Report issued in International Application No. PCT/EP2016/054672 dated Jun. 1, 2016.

* cited by examiner

*Primary Examiner* — Michael F Pepitone
(74) *Attorney, Agent, or Firm* — McDonnell Boehnen Hulbert & Berghoff LLP

(57) ABSTRACT

The invention relates to a polymerizable dental material containing a catalyst paste (A) and a base paste (B), wherein the catalyst paste (A) contains at least one organic peroxygen compound, at least one radically polymerizable organic (meth)acrylic monomer and at least one filler, and wherein the base paste (B) contains at least one radically polymerizable organic (meth)acrylic monomer, an amine as co-initiator of the radical polymerization, at least one filler and at least one salt-like, water-soluble, powdery reduction agent dispersed therein, wherein the catalyst paste (A) and/or the base paste (B) contains at least one phase transfer catalyst that is selected from the group consisting of the ammonium, phosphonium and/or sulfonium salts that contain an inorganic or organic anion, provided that the phase transfer catalyst—in the event of organic anions—contains only those having 1-4 carbon atoms, and that anions of sulfinic acids are precluded.

24 Claims, No Drawings

POLYMERIZABLE DENTAL MATERIAL WITH A PHASE TRANSFER CATALYST

CROSS REFERENCE TO RELATED APPLICATIONS

The present application claims the benefit of German Patent Application No. 10 2015 103 427.1 filed Mar. 9, 2015 the entire contents of which are incorporated entirely herein by reference.

The present invention relates to a polymerizable dental material containing at least one catalyst paste and at least one base paste containing selected components respectively.

The polymerizable dental materials of the present invention can be used in therapeutic treatment for the buildup and the reconstruction of decayed, natural dental substance. In particular, when a tooth stump that secures a firm anchoring of the core in the jaw is still present, these dental materials are used to build up the stump of severely decayed teeth. For example, tooth stumps of severely decayed teeth can be built up by applying dental material; alternatively, large cavities can be closed in the natural tooth substance in order to obtain satisfactory results for the patient from a functional point of view. Consequently, the dental material materials must have a sufficiently high level of hardness. Additional preferred forms of use are the mounting of prosthetic materials such as, for example, crowns, bridges, inlays, onlays or veneers. In particular, it is critical for both applications that the dental materials adhere to the tooth material that is still present to a satisfactory degree, as the dental materials applied are exposed to powerful forces during chewing. The generic polymerizable dental materials can meet various requirements depending on their planned use.

Polymerizable dental materials used to build up missing tooth substances are also called core build-up materials. Preferably, hydrophobic monomers are used for such core build-up materials. In order to facilitate the application by the treating dentist it is preferred that these core build-up materials are present in paste-like form so that the dentist can build up the tooth core in the mouth of the patient and model it at least roughly. In order to ensure a high degree of strength and sufficient polymerization of the polymerizable monomers, when purely light-curing composites were used, frequently only a thin layer of composite (polymerizable dental material) was applied to the tooth core, which was then cured with a treatment lamp (i.e. polymerized) and subsequently, another layer was applied. In particular, such a layer build-up is indispensable in the case of purely light-curing materials, but at any rate, extremely time-intensive and for this reason, disadvantageous for the treating dentist and also for the patient.

A further application of polymerizable dental materials relates to so-called polymerizable composite cements. In particular, these are used for mounting prosthetic materials such as tooth crowns and other tooth replacement materials. Finally, polymerizable dental materials can also be taken into consideration as so-called bulk fill composites for filling tooth cavities.

If the polymerizable dental material is applied to the natural tooth substance, a firm connection must be established between the composite material applied and the natural tooth substance. By using adhesives, such an adhesion can be achieved by applying the adhesive to the tooth substance for improved wettability which thus leads to an improved adhesion of the material that is applied to the tooth substance. Preferably, the adhesives are used in liquid form so that these can be distributed on the tooth substance easily and evenly.

In order to establish the adhesion promotion between the material applied and the natural tooth substance described above, essentially three steps are performed.

Initially, as the first step, the natural tooth substance is etched, which roughens the surface of the tooth substance, in particular, the dental enamel. With respect to the interior tooth substance, in particular, the dentin, the etching can dissolve minerals of the collagen composite of the natural tooth substance, in particular the dentine. Subsequently, primarily open dentinal tubules and exposed collagen fibers remain on the surface of the tooth.

For sufficient adhesion between the dental material applied and the natural tooth substance it is necessary to coat the etched tooth surface by means of a so-called primer in a second step. So that this coating sufficiently adheres to the hydrophilic collagen fibers, the primer contains hydrophilic monomers, for example, 2-hydroxyethyl methacrylate (HEMA), which can penetrate through the exposed collagen fiber composite. Subsequently, the primer cures.

As the polymerizable dental materials to be applied typically contain hydrophobic monomers, a direct application of the polymerizable dental material to the hydrophilic primer would not achieve sufficient adhesion between the two materials. For this reason, an additional layer, a so-called bonding must first be applied as the third step in order to achieve sufficient adhesion between the polymerizable dental material and the natural tooth substance.

The steps described can be performed using different, separately packaged substances that are applied in several treatment steps.

For the etching (first step) a 35% phosphoric acid is typically used which is applied to the natural tooth substance and which remains there for up to 20 seconds. Subsequently, the acid was removed by rinsing it off with water. The treated sites are then dried with air. As the next substance, a primer (second step) can be applied to the etched tooth substance. Subsequent to its polymerization, the bonding, (third step) is applied as a final step, which likewise cures, i.e. polymerizes.

In particular, the lengthy treatment time of the application of three substances (phosphoric acid, primer, bonding) as described is disadvantageous, because of the treatment steps that have to be performed: etch, rinse with water, blow dry, apply primer, polymerize primer, apply bonding and polymerize bonding. Furthermore, it is disadvantageous that three different substances must be stocked in three different packages.

For this reason, products were developed that combine one or more of the steps described above in one substance or in a mixture of substances.

In one variant, first the etching is performed and subsequently, a product is applied that comprises hydrophilic and also hydrophobic monomers and for this reason, assumes the function of the primer and the bonding (so-called priming+ bonding systems).

In another variant, the etching is combined with the primer in such a way that phosphoric acid groups are provided at the hydrophilic monomers of the primer that etch the natural tooth substance. After the polymerization of this primer with phosphoric acid groups, the bonding is applied.

Both variants make it possible to save treatment steps and only two separately packaged substances are still required.

A refinement of the adhesives described above is represented by the so-called all-in-one adhesives, one-step adhesives, or also one-step adhesion promotors. These combine the three steps described above in a single product. In other words, these all-in-one adhesives combine etching, the primer and the bonding in a single treatment step. For this reason, using the all-in-one adhesives achieves a significant saving of time for the treating dentist and the patient.

However, during the treatment with all-in-one adhesives and in some cases also with priming+bonding systems it has been found to be problematic that the phosphoric acid groups of the monomers it contains do not only etch the natural tooth substance, but can also react with the polymerizable dental materials that are to be applied and can interfere with their curing.

The polymerizable dental materials to be applied must cure at the moderate temperatures in the oral cavity of the patient already, i.e. polymerize. Any heating of the polymerizable dental material in order to initiate a polymerization (to typically 80° C.) would be extremely unpleasant for the patient and is therefore out of the question.

For the reasons cited above, to polymerize the polymerizable dental material, initiators that cure quickly at moderate temperatures are generally used for chemical curing, namely, an ambient mouth temperature of approx. 36° C. For this reason, primarily redox initiators that trigger a polymerization of the dental material are used. Typically, a redox initiator system is used that comprises a peroxygen compound together with a co-initiator, e.g. an aromatic amine. Thereby the peroxygen compound is provided in one of the pastes of the polymerizable dental material (the so-called catalyst paste), and the co-initiator in the other paste of the polymerizable dental material (the so-called base paste). When the peroxygen compound and the co-initiator come in contact when the pastes are mixed, a redox reaction takes place that supplies the radicals needed for the polymerization of the organic monomers contained in the dental material. The two pastes are stored separately in order to ensure a long shelf-life.

An example of dental materials with particularly good optic and mechanical properties is described in WO 2014/033 280 A1. These dental materials can be cured with different initiator systems with initiator systems based on barbituric acid derivatives being preferably used. These preferred initiator systems include a metal compound, a (pseudo) halide compound and a barbituric acid derivative. Optionally photoinitiators and/or co-initiators as well as an organic perester compound can be used. The (pseudo) halide compounds used in this initiator system can contain besides (pseudo) halide anions any cations, including among others ammonium cations.

This publication also discloses other initiator systems that can be used in addition to or alternatively to the preferred barbiturate system. These are redox initiator systems consisting of a combination of inorganic peroxide, for example of sodium or potassium peroxodisulphate, combined with alkaline or earthalkaline toluolsulfinate or with alkaline or earthalkaline sulfite. Also, redox initiator systems are disclosed, which include at least an amine and at least an organic peroxide, and optionally photoinitiators and/or co-initiators.

This prior art does not disclose a combination of organic peroxide, amine, pulverulent reducing agent and ammonium salt. It does also not disclose that the alkaline or earthalkaline sulfites, which are combined with inorganic peroxide in the redox initiator system, are existent in the form of powders. This prior art does not disclose the use of phase transfer catalysts in combination with a pulverulent reducing agent, which together with the remaining ingredients of a redox initiator system result in a rapid and complete curing of the monomers under mouth conditions.

Purely light-curing dental materials that have a polymerization initiated by exposure to light are also used in the practice of a dentist. Thereby, it is disadvantageous that the treating dentist has to apply these materials in thin layers, as the irradiated light is unable to penetrate into deeper layers of the dental material. As a result, the treatment takes significantly more time.

In order to combine the advantages of chemical curing with those of light-curing, materials were also developed that contain both initiator systems and thus have dual-hardening properties. Examples of such two-component dental materials can be found in prior art, for example, in EP 1 790 323 A1, EP 2 237 763 B1 or EP 2 374 445 A2.

If all-in-one adhesives and the polymerizable dental materials described having a redox initiator consisting of a peroxygen compound and a co-initiator are used for the treatment, however, the polymerization is generally insufficient at the boundary layer of the adhesive and the polymerizable dental material. This is explained thereby, that the carboxylic, acid phosphoric acid or phosphonic acid groups contained in the all-in-one adhesive protonate the amines used as co-initiators, as a result of which these are converted into an ammonium compound. Thereby, the actually desired redox reaction of the (original) amines with the percompound for initiating the polymerization reaction is prevented, and at the boundary layer of adhesive and polymerizable dental material, the dental material does not cure sufficiently.

This problem also occurs in dual-hardening dental masses when the light of the treatment lamp does not penetrate to the bottom of the cavity at which the boundary layer to the adhesive is located, due to the thickness of the layer.

In such cases, the use of a well-established polymerizable dental material with a redox initiator together with an all-in-one adhesive results in a reduction of the adhesion of the dental material on the adhesive. For this reason, the treating dentist can use such adhesives only in connection with an additional activator that takes on the self-curing, or he must resort to other dental materials (for example, exclusively light-curing dental materials), which have, however, the disadvantages described above, in particular, require a longer treatment time.

To improve the adhesive effect between the tooth substance and the polymerizable dental materials with redox initiator, EP 2 409 997 A1 describes a composition that penetrates the tooth substance and uses the moisture contained in the tooth substance to achieve an accelerated curing of the dental material. The composition described contains a mixture of monomers, an inorganic peroxide, a reduction agent and a polymerization accelerator. The polymerization catalyst is dissolved by the moisture on the surface of the tooth substance, as a result of which the polymerization/curing at the boundary adhesive layer and within the curable composition is improved. Examples for such an accelerator are water-soluble sulfites that are suitable as co-initiators, but also ammonium salts such as tetramethylammonium salt and the tetraethylammonium salt of benzol sulfonic acid. According to the examples in EP 2 409 997 A1, the polymerization accelerator is in the base paste.

EP 1 780 223 B1 describes an adhesive for dentistry, wherein a polymerization accelerator, namely a water-soluble sulfite is added as an additional co-initiator. The sulfite is dispersed in the polymerizable monomer and dissolved at the boundary layer to the natural tooth substance by the moisture in the tooth. Due to the additional reduction effect of the sulfite, an improved curing of the polymerizable dental material results at the boundary layer between the tooth and the polymerizable dental material, which improves the bonding effect. The use of phase transfer catalysts is not mentioned in this document.

EP 2 554 154 A1 describes a kit consisting of an adhesive and a curable composition with a high degree of adhesion and stability for dentistry. In contrast to EP 1 780 223 B1, in which the water-soluble reduction agent (sodium sulfite) is used exclusively in dental adhesives that contain hydrophilic monomers (HEMA), in EP 2 554 154 A1, hydrophobic monomer mixtures are used. The curable composite described in EP 2 554 154 A1 is therefore suitable for use as core build-up material, in contrast to the products in EP 1 780 223 B1. The pertaining adhesive of the kit cited above includes a monomer mixture, water and an amine-based sulfur-free reduction agent. The core build-up material also includes a monomer mixture, a water-soluble, sulfur-containing reduction agent, an organic peroxide and an amine-based, sulfur-free reduction agent. Here also the use of phase transfer catalysts is not disclosed.

It is a disadvantage of the solution described in EP 2 554 154 A1 that a special adhesive is required for applying the core build-up material that is also supplied in the kit, which contains an additional amine as reduction agent which reduces the etching effect on the tooth surface of the phosphoric acid methacrylate (e.g. MDP) that is likewise contained in the adhesive, by means of a partial neutralization.

Based on that, it is the objective of the present invention to provide a polymerizable dental material that can be used with all popular adhesives, in particular, the priming+bonding systems and the all-in-one adhesives without having any of the disadvantages described above. In particular, it is the objective of the invention to provide a polymerizable dental material that achieves sufficient curing and thus an improved adhesive bonding and simultaneously, a long shelf-life of the paste-like masses (>1 year, preferably >2 years) at the boundary layer to all adhesives, in particular, the priming+bonding systems and the all-in-one adhesives.

This problem is solved by the features of claim 1 thereby, that the polymerizable dental material contains a catalyst paste (A) and a base paste (B). The catalyst paste includes at least one organic peroxygen compound, at least one filler and at least one radically polymerizable organic (meth)acrylic monomer. The base paste contains at least one radically polymerizable organic (meth)acrylic monomer, at least one filler, an amine as co-initiator of the radical polymerization and at least one salt-like, water-soluble, powdery reduction agent (hereinafter also: reduction agent) that is dispersed in base paste (B). Furthermore, in at least one catalyst paste and/or base paste at least one phase transfer catalyst is provided that is an ammonium, a phosphonium and/or a sulfonium salt that contains an inorganic or organic anion with the provision that the phase transfer catalyst—in the case of organic anions—has only those with 1-4 carbon atoms and that anions of sulfinic acids are precluded.

By using the phase transfer catalyst according to the invention, the adhesion between the cured dental material and the adhesive is indirectly improved. This can be explained thereby, that the salt-like, water-soluble and powdery reduction agent is dissolved at the boundary layer to the adhesive and can then be incorporated into the organic (meth)acrylic monomer mass in order also achieve an acceleration of the polymerization by reacting with the peroxygen compound. Due to the separation of the polymerizable dental material into at least one catalyst paste and at least one base paste, a long shelf-life is achieved. The polymerizable dental material that cures quickly under the conditions in the mouth (appropriate temperature and moisture) is produced by mixing these individual components.

Preferably, the proportion of the phase transfer catalyst in the catalyst paste and/or the base paste, relative to the total mass of the catalyst paste and/or the base paste is 0.01 to 5.0% by weight, preferably 0.01 to 2.0% by weight, particularly preferred, 0.05 to 1.0% by weight and very particularly preferred, 0.05 to 0.5% by weight.

The cited weight proportion of the phase transfer catalyst in the catalyst paste and/or the base paste relative to the total mass of the catalyst paste and/or the base paste must be selected to be so low that the curing of the polymerizable dental material at the boundary surface to the adhesive does not progress so fast that any finishing of the dental material is made more difficult or even made impossible. This is especially important if the product can also be applied in the root canal, because otherwise, the insertion of the root post can become impossible due to an early blockage of the root canal. At the same time, the cited weight proportion should be selected to be so high that the polymerization at the boundary layer to the adhesive progresses at approximately the same speed as the polymerization within the dental mass, to avoid a detachment of the otherwise hardened mass from the tooth substance.

In light of the shelf-life of the polymerizable dental material, it has been shown to be advantageous when the phase transfer catalyst is provided in the at least one catalyst paste only. This is explained thereby, that residues of moisture in the pastes cannot be precluded and, in particular, moisture can penetrate the packaging of the pastes during storage. This moisture can dissolve the reduction agent dispersed in the base paste and thereby activate redox reactions. Should the phase transfer catalyst be present already in the base paste together with the reduction agent, it cannot be precluded that in combination with any existing moisture, an enhanced integration of the reduction agent into the organic (meth)acrylic monomer takes place, and the monomer reacts with the reduction agent. Even atmospheric oxygen trapped in the base paste can react with the reduction agent as oxidation agent and thereby trigger a polymerization of the organic (meth)acrylic monomer during storage. This would render the base paste useless.

If the phase transfer catalyst is provided in the base paste, it is advantageous to take steps that prevent a premature conversion of reduction agent, phase transfer catalyst and the (meth)acrylic monomer in order to lengthen the shelf-life of the base paste. For this, it has been shown to be advantageous when a desiccant is added to the base paste that binds any water that penetrates or is contained in the base paste during storage and thus prevents dissolution of the reduction agent. Alternatively or additionally, a base can be added to the base paste that prevents a redox reaction of the reaction agent with atmospheric oxygen or at least slows such down.

Examples of desiccants include: silica gel, zeolites, aluminum oxide, calcium oxide and/or calcium sulfate and magnesium oxide and/or magnesium sulfate.

In a preferred embodiment of the invention, the phase transfer catalyst is contained in the catalyst paste. This has been shown to be particularly favorable in light of the shelf-life, as the potential activation of the reduction agent present in the base paste with the phase transfer catalyst and a subsequent reaction of the reduction agent with the atmospheric oxygen can thereby be prevented, as described above.

According to the invention, the term reduction agent refers to a substance that forms a redox system in combination with the peroxygen compound that is suitable for initiating a radical polymerization of the polymerizable (meth)acrylic monomer. Further, the reduction agent can prevent a reaction of a radical, growing polymer chain with the di-radical oxygen which can lead to an interruption of the polymerization reaction when the reduction agent reacts with the oxygen after dissolution.

Within the scope of the present invention, the term water-soluble refers to a substance that has a solubility of at least 10 g/l, preferably at least 15 g/l, particularly preferred, at least 30 g/l, and very particularly preferred, at least 50 g/l in distilled water at a temperature of 25° C.

Preferably, the reduction agent is selected from the group consisting of sulfites, in particular, from the group of alkali metal sulfites, alkaline earth metal sulfites, $(NH_4)_2SO_3$, or hydrogen sulfites (bisulfites), disulfites, thiosulfites, thionates and dithionites, in particular, the alkali metal salts or alkaline earth metal salts thereof. It is particularly preferred when sodium sulfite is used as reduction agent. The cited reduction agents have shown to be particularly suitable for the present invention as these have low solubility in the organic monomer and are dispersed in the base paste, but can be integrated particularly well into the organic monomer by the phase transfer catalyst used according to the invention.

The weight proportion of the reduction agent relative to the total mass of the at least one base paste is preferably less than 10 percent by weight, particularly preferred, less than 5 percent by weight, and very particularly preferred, 2±1 percent by weight. Too much reduction agent leads to a level of solubility of the polymerizable mass that is too high so that after curing, washing with saliva can create a porous product that has a significantly reduced mechanical strength. At the same time, the cited weight proportion must be selected to be high enough so that the polymerization of the dental material occurs as intended, even at the boundary layer to the adhesive.

In the at least one base paste, an amine is provided as co-initiator that is suitable—regardless of the reaction agent—to initiate a polymerization reaction of the organic (meth)acrylic monomer with the peroxygen compound.

Generally, the co-initiator is selected from the group consisting of the primary, secondary and/or tertiary amines, in particular, the secondary amines and/or the tertiary amines. Examples of suitable secondary amines and/or suitable tertiary amines include o-tolyldiethanolamine, m-tolyldiethanolamine, p-tolyldiethanolamine, N-methylaniline, N-methyl-o-toluidine, N-methyl-m-toluidine, N-methyl-p-toluidine, methyl-2-anisidine, methyl-3-anisidine, methyl-4-anisidine, N,N,-dimethyl-o-toluidine, N,N,-dimethyl-m-toluidine and/or N,N,-dimethyl-p-toluidine.

The weight proportion of the co-initiator that is used relative to the total mass of the at least one base paste is preferably less than 5 percent by weight, particularly preferred, less than 2 percent by weight and very particularly preferred, 1±0.5 percent by weight.

Preferably the peroxygen compound is a peroxide, a peroxide ester, in particular, a diacyl peroxide, a dialkyl peroxide, a peroxy ketal, a peroxy ketone or a hydrogen peroxide. It is critical for the peroxygen compound used that the peroxygen compound forms a redox system in combination with the reduction agent and the co-initiator that is suitable for initiating a radical polymerization of the organic (meth)acrylic monomer. In other words, the redox potentials of the peroxygen compound and the reduction agent or the co-initiator must be coordinated in such a way that a redox reaction will occur between the two creating radicals that start a polymerization of the (meth)acrylic monomer.

In a preferred embodiment, the organic peroxygen compound is a diacyl peroxide, in particular, a benzoyl peroxide or its halogenated derivatives, preferably dibenzoyl peroxide.

The weight proportion of the peroxygen compound relative to the total weight of the at least one catalyst paste is preferably less than 5 percent by weight, particularly preferred, less than 2 percent by weight, particularly preferred, less than 1 percent by weight and very particularly preferred, 0.8±0.2 percent by weight.

The cited redox initiator systems can also be complemented with at least one further initiator system. Thus, for example, at least one photoinitiator and/or at least one radical starter that can be activated thermally, for example, azo compounds can be provided in the polymerizable dental material.

These additional initiator systems can be provided in the at least one catalyst paste and/or the at least one base paste. The person skilled in the art is familiar with initiator classes of this type.

A preferably provided photoinitiator makes it possible for the practitioner to achieve curing ahead of schedule at any time by using a polymerization lamp. Customarily, photoinitiator systems consisting of camphorquinone and an aromatic amine are used to light-cure dental materials. Such a mixture generates radicals when irradiated with blue light having a wavelength in the range of 470 nm that cure the material completely in less than one minute. The photoinitiator can be present in the catalyst paste and/or in the base paste.

For example, alpha diketones such as camphorquinone, in particular, DL-camphorquinone in combination with secondary and tertiary amines such as, for example, ethyl-4-dimethylaminobenzoate or (2-ethylhexyl)-4-dimethylaminobenzoate, and where applicable, mono and bisacylphosphine oxides, such as 2,4,6-trimethyl-benzoyl diphenylphosphine oxide and bis-(2,6-dichlorobenzoyl)-4-n-propylphenyl-phosphine oxide and benzaldehyde, are suitable as photoinitiators.

The weight proportion of the photoinitiator components relative to the total weight of the at least one base paste, or the at least one catalyst paste is preferably less than 10 percent by weight, preferably less than 5 percent by weight, particularly preferred, less than 2 percent by weight, and very particularly preferred, less than 1 percent by weight.

In particular, for the use of the polymerizable dental material as core build-up material and as polymerizable composite cement it is preferred when a redox initiator system is provided as well as a photoinitiator. Such polymerizable dental materials are also called dual-hardening.

In a preferred embodiment of the invention, the (meth)acrylic monomer is selected from the group consisting of the acrylates or methacrylates (collectively: (meth)acrylates) and/or acrylamides or methacrylamides (collectively: (meth)acrylamides). Thereby, the bi or higher functional acrylic acid and methacrylic acid compounds such as (meth)acrylic acid ester and also mono-functional (meth)acrylic acid compounds such as (meth)acrylic acid esters can be provided.

Within the scope of the present invention, the (meth)acrylic monomers can be individual compounds, oligomers and/or polymers that contain at least one polymerizable group derived from (meth)acrylic acid such as a (meth) acrylate or a (meth)acrylamide group.

Within the scope of the present invention, single compounds refer to compounds that do not have any recurring structural units.

Within the scope of the present invention, oligomers refer to compounds that have two to ten recurring structural units.

Within the scope of the present invention, polymers refer to compounds that have more than ten recurring structural units.

The preferably used radically polymerizable organic (meth)acrylic monomers include acrylates or methacrylates containing aromatic groups, acrylates or methacrylates containing aliphatic groups, acrylates or methacrylates containing oligo and polyether groups, acrylates or methacrylates containing oligo and polyester groups, acrylates or methacrylates containing urethane groups, or combinations of two or more of these monomers.

Examples of suitable (meth)acrylates include bisphenol-A-di(meth)acrylate, bis-GMA (an addition product consisting of methacrylic acid and bisphenol-A-diglycidyl ether), ethoxylated bisphenol-A-di(meth)acrylate, UDMA (an isomer mixture consisting of di-2-methacryloxyethyl-2,2,4-trimethylhexamethylene dicarbamate and di-2-(meth)-acryl-oxyethyl-2,4,4-trimethylhexamethylene dicarbamate), 2-hydroxyethylmethacrylate (HEMA) and/or gylcerin-1,3-dimethacrylate (GDMA), as well as ethyl(meth)acrylate, isopropyl(meth)acrylate, n-butyl-(meth)-acrylate, isobutyl (meth)acrylate, tetrahydro-furfuryl(meth)acrylate, glycidyl (meth)-acrylate, 2-methoxyethyl-(meth)acrylate, 2-ethoxy-ethyl(meth)-acrylate, 2-methoxy-ethyl(meth)acrylate, 2-ethylhexyl(meth)-acrylate, 2-hydroxy-1,3-di(meth)-acry-loxy propane, neopentyl glycol di(meth)acrylate, 1,3-butanediol-di(meth)acrylate, 1,4-butanedioldi(meth)acrylate, 1,6-hexanediol-di(meth)acrylate, 1,8-octanediol-di-(meth) acrylate, 1,10-decanedioldi(meth)acrylate, 1,12-dodecane-dioldi(meth)acrylate, 1,14-tetradecanedioldi(meth)acrylate, 1,16-hexa-decanedioldi(meth)acrylate, trimethylolpropane tri(meth)acrylate, trimethylolethane tri(meth)acrylate, pentaerythritol tri(meth)acrylate, dipentaerythritol penta(meth)-acrylate, dipentaerythritol hexa(meth)acrylate, trimethylol-methane tri(meth)acrylate, pentaerythritol tetra(meth) acrylate, tetraethylene glycol di(meth)acrylate, mono, oligo, or polyethylene glycol di(meth)acrylate, e.g. ethylene glycol di(meth)acrylate, diethylene glycol di(meth)acrylate and triethylene glycol di(meth)acrylate, mono, oligo, or polypropylene glycol di(meth)acrylate, and mono or polybutylene glycol di(meth)acrylate, in particular, mono or polytetramethylene glycol di(meth)acrylate, whereby the polyalkylene glycol derivatives include those with branched as well as those with linear structures.

Additionally (meth)acrylates having urethane group(s) are also included as examples of components of the cited mixtures for (meth)acrylates. Suitable examples include di-2-(meth)acryloxyethyl-2,2',4-trimethylhexamethylene dicarbamate, di-2-(meth)acryl-oxyethyl-2,4,4'-trimethylhexamethylene dicarbamate and 1,3,5-tris[1,3-bis{(meth)-acryloyloxy}-2-propoxycarbonyl amino-hexane]-1,3,5-(1H, 3H,5H)triazine-2,4,6-trion. Additionally, by way of example a (meth)acrylate of a urethane oligomer is cited that is derived from 2,2'-di(4-hydroxy-cyclohexyl)propane, 2-oxepanone, hexamethylene diisocyanate and 2-hydroxy-ethyl (meth)acrylate, and a (meth)acrylate of a urethane oligomer that is derived from 1,3-butanediol, hexamethylene diisocyanate and 2-hydroxy-ethyl(meth)-acrylate. These (meth) acrylates can be used in the polymerizable dental material by themselves or as a mixture of two or more in combination.

Very particularly preferred, radically polymerizable organic (meth)acrylic monomers that are free of structural units with aromatic residues are used, in particular, those radically polymerizable organic (meth)acrylic monomers that do not contain any structural units that are derived from Bisphenol A.

According to the invention the (meth)acrylic monomer is used in the base paste (B) and in the catalyst paste (A).

The phase transfer catalyst is selected from the group consisting of ammonium salts, phosphonium salts and/or sulfonium salts with inorganic or organic anions, whereby in the case of organic anions, the phase transfer catalyst contains only those with 1-4 carbon atoms, and whereby anions of sulfinic acid are precluded. The salts can be used in hydrous or anhydrous form.

It is further preferred when the cation of the ammonium salt is $NR_1R_2R_3R_4$, whereby $R_1$, $R_2$, $R_3$ and $R_4$—independent of each other—mean $C_1$ to $C_{20}$, in particular, $C_1$ to $C_{10}$, preferably $C_4$ alkyl, $C_1$ to $C_{20}$, in particular, $C_1$ to $C_{10}$, preferably $C_4$ alkyl halogenide, $C_1$ to $C_{20}$, in particular, $C_1$ to $C_{10}$, preferably $C_4$ alkyloxy, in particular, benzethonium, $C_2$ to $C_{20}$, in particular, $C_2$ to $C_{10}$, preferably $C_4$ alkenyl, $C_2$ to $C_{20}$, in particular, $C_2$ through $C_{10}$, preferably $C_4$ alkenyloxy, $C_2$ through $C_{20}$, in particular, $C_2$ through $C_{10}$, preferably, $C_4$ alkinyl, $C_2$ to $C_{20}$, in particular, $C_2$ to $C_{10}$, preferably, $C_4$ alkinyloxy, $C_2$ to $C_{20}$, in particular, $C_2$ to $C_4$ alkyl ester, particularly preferred, methyl ester, aryl, preferably phenyl, aryloxy, aralkyl, preferably benzyl, aralkyloxy, alkylaryl, alkylaryloxy, wherein preferably at least one of the residues $R_1$, $R_2$, $R_3$ or $R_4$ is at least one $C_1$ residue, preferably at least one $C_2$ residue, particularly preferred at least one $C_3$ residue, and very particularly preferred, at least one $C_4$ residue. The cited residues also include possible constitution and stereo isomers. Ammonium salts with at least one $C_4$ residue are particularly preferred for hydrophobic core build-up materials.

In one particular embodiment of the invention, several of the cited residues can also be present in chemically bonded form. Thereby, the nitrogen atom of the ammonium salt is integrated into a cyclical compound, namely a heterocycle. Examples of heterocycles that are suitable for the base body include aziridines, azetidines, azolidines, azinanes, azepanes, azirines, azetes, azoles, azines, azepines, pyrazoles, imidazoles, benzimidazoles, imidazolines, indoles, chinolines, isochinolines, purines, pyrimidines or oxazoles. These can be used as correspondingly substituted compounds as ammonium salts. Thereby, it must be taken into consideration that at a corresponding redox potential, primary, secondary and tertiary amines can react with the peroxygen compound. For this reason it is preferred to use only those heterocyclic compounds cited above that do not contain any primary, secondary and tertiary amines.

Suitable examples for heterocyclic ammonium salts include N-(allyloxycarbonyloxy)succinimide, 3-benzyl-5-(2-hydroxyethyl)-4-methylthiazolium chloride, 1-butyl-2,3-dimethylimidazolium chloride, 1-butyl-2,3-dimethyl-imidazoliumhexafluoro phosphate, 1-butyl-2,3-dimethylimidazolium tetrafluoroborate, 1,3-didecyl-2-methylimidazolium chloride, 1-ethyl-2,3-dimethylimidazolium ethyl sulfate, 3-ethyl-5-(2-hydroxyethyl)-4-methylthiazolium bromide, hexacylpyridinium bromide, hexadecylpyridinium chloride, 5-(2-hydroxyethyl)-3,4-dimethylthiazolium iodide, 1-methylimidazolium hydrogen sulfate, methylviologen dichloride and 1,2,3-trimethyl imidazolium salts.

Even commercially available phase transfer catalysts can be used with the present invention. Suitable examples include Aliquat® 336, a quaternary ammonium salt, wherein $R_1$ is methyl and $R_2$, $R_3$ and $R_4$ is octyl and/or decyl, wherein primarily octyl is present, or Arquad® 2HT-75.

According to the invention, ammonium salts are particularly preferred phase transfer catalysts.

A preferred cation of the phosphonium salt is $PR_1R_2R_3R_4$ wherein $R_1$, $R_2$, $R_3$ and $R_4$—independent of each other—mean $C_1$ to $C_{20}$, in particular, $C_1$ to $C_{10}$, preferably $C_4$-alkyl, $C_1$ to $C_{20}$, in particular, $C_1$ to $C_{10}$, preferably $C_4$ alkyl halogenide, $C_1$ to $C_{20}$, in particular $C_1$ to $C_{10}$, preferably $C_4$ alkyloxy, in particular, benzethonium, $C_2$ to $C_{20}$, in particular, $C_2$ to $C_{10}$, preferably $C_4$ alkenyl, $C_2$ to $C_{20}$, in particular, $C_2$ to $C_{10}$, preferably $C_4$ alkenyloxy, $C_2$ to $C_{20}$, in particular $C_2$ to $C_{10}$, preferably $C_4$ alkinyl, $C_2$ to $C_{20}$, in particular, $C_2$ to $C_{10}$, preferably $C_4$ alkinyloxy, $C_2$ to $C_{20}$, in particular, $C_2$ to $C_4$ alkyl ester, particularly preferred, methyl ester, aryl, preferably phenyl, aryloxy, aralkyl, preferably benzyl, aralkyloxy, alkylaryl, alkylaryloxy, wherein preferably at least one of the residues $R_1$, $R_2$, $R_3$ or $R_4$ is at least one $C_1$ residue, preferably at least one $C_2$ residue, particularly preferred, at least one $C_3$ residue, and very particularly preferred, at least one $C_4$ residue.

A preferred cation of the sulfonium salt is $SR_1R_2R_3$, wherein $R_1$, $R_2$ and $R_3$-independent of each other—mean $C_1$ bis $C_{20}$, in particular, $C_1$ through $C_{10}$, preferably $C_4$ alkyl, $C_1$ to $C_{20}$, in particular, $C_1$ to $C_{10}$, preferably $C_4$ alkyl halogenide, $C_1$ to $C_{20}$, in particular, $C_1$ to $C_{10}$, preferably $C_4$ alkyloxy, in particular, benzethonium, $C_2$ to $C_{20}$, in particular, $C_2$ to $C_{10}$, preferably $C_4$ alkenyl, $C_2$ to $C_{20}$, in particular, $C_2$ to $C_{10}$, preferably $C_4$ alkenyloxy, $C_2$ to $C_{20}$, in particular, $C_2$ to $C_{10}$ preferably $C_4$ alkinyl, $C_2$ to $C_{20}$, in particular, $C_2$ to $C_{10}$, preferably $C_4$ alkinyloxy, $C_2$ to $C_{20}$, in particular, $C_2$ to $C_4$ alkyl ester, particularly preferred, methyl ester, aryl, preferably phenyl, aryloxy, aralkyl, preferably benzyl, aralkyloxy, alkylaryl, alkylaryloxy, wherein preferably, at least one of the residues $R_1$, $R_2$ or $R_3$ is at least one $C_1$ residue, preferably at least one $C_2$ residue, particularly preferred, at least one $C_3$ residue, and very particularly preferred, at least one $C_4$ residue.

The anion of the ammonium salt, the phosphonium salt and/or the sulfonium salt is an inorganic anion or a selected organic anion with 1 to 4 carbon atoms and with the exception of the anion of sulfinic acid. The later anions have a level of redox activity that is too high and lead to dental masses with an insufficient shelf-life. Organic anions with 1-4 carbon atoms make the phase transfer catalyst sufficiently hydrophilic so that a sufficiently fast transition of the dissolved reduction agent into the hydrophilic phase at the boundary layer to the adhesive is possible and after the start of this phase, the exchange of the anion with the hydrophilic reducing anion is facilitated, which must then be returned to the organic phase again.

According to the invention, phase transfer catalysts that do not contain any anions of sulfonic acids are particularly preferred.

According to the invention, very particularly preferred phase transfer catalysts are those that contain inorganic anions.

Examples for preferred anions are anions selected from the group consisting of halogenides, hydroxides, anions of inorganic acids, pseudohalogenide anions or halogen complexes of aluminate, borate, silicate or phosphate, or anions of short-chained, organic acids with 1 to 4 carbon atoms, for example, of carboxylic acids with one to four carbon atoms, except for the anions of sulfinic acids.

Particularly preferred anions are fluoride, chloride, bromide, iodide, hydroxide, sulfate, hydrogen sulfate, phosphate, hydrogen phosphate, dihydrogen phosphate, phosphonate, borate, chlorate, perchlorate, nitrite, nitrate, hydrogen carbonate, carbonate, tetrafluoroborate, tetrachloroaluminate, hexafluorosilicate, hexachlorophosphate, formate, acetate, butyrate, fumarate, maleate, glutarate, lactate, malate, malonate, oxalate pyruvate or tartrate.

The following anions have shown to be particularly favorable: hydrogen sulfate, sulfate, dihydrogen phosphate, chloride and tetrafluoroborate.

Overall, particularly advantageous phase transfer catalysts have relatively high hydrophilic properties. This explained thereby, that the polar, watery phase containing reduction agent is relatively small at the boundary layer to the adhesive applied to the natural tooth substance, compared with the hydrophobic dental material mass. In other words, only a very small part of the phase transfer catalyst is present in the watery phase. Correspondingly, the high level of hydrophilicity has the effect that a significant proportion is also in the watery phase and thus accelerates the integration of the reduction agent into the hydrophobic monomer mass. Correspondingly, the use of polar substances as phase transfer catalysts is preferred, whereby the cations and the anions are preferably characterized as rather hard according to the HSAB concept ("Hard and Soft Acids and Bases"). Such hard cations are preferably ammonium ions with relatively short-chained ($C_1$ to $C_4$) residues, whereby individual longer residues (up to $C_{20}$) have shown to be unproblematic. The same applies to the anions used, which are preferably hard, for example, tetrafluoroborate, while soft anions, for example, hexafluorophosphate, have shown to be less suitable.

In a very particularly preferred embodiment, the phase transfer catalyst includes tetrabutylammonium hydrogen sulfate, tetrahexylammonium hydrogen sulfate, tetramethylammonium hydrogen sulfate, tetraphenylphosphonium chloride, tetrabutylphosphonium chloride, bis-[tetrakis(hydroxymethyl)phosphonium] sulfate, 1,2,3-trimethylimidazolium methyl sulfate, 1,2,3-trimethylimidazolium ethyl sulfate, 1-ethyl-2, 3-dimethyl-imidazolium ethylsulfate, cetyltrimethylammonium hydrogen sulfate, (vinylbenzyl) trimethylammonium chloride, tetrabutylammonium chloride, tetrabutylammonium acetate, tetrabutylammonium hexafluorophosphate and/or tetrabutylammonium tetrafluoroborate.

Inorganic or organic materials can be used as fillers for the catalyst paste and the base paste. The fillers can be reinforcing fillers or non-reinforcing fillers or mixtures of such.

Reinforcing fillers are particularly suited for highly disperse, active fillers having a BET surface of at least 50 m²/g. Those with an individual particle size in the nanometer range are particularly suitable. These can be present as aggregates and/or agglomerates. Preferred reinforcing fillers are substances that are selected from the group consisting of aluminum hydroxide, zinc oxide, titanium dioxide, zirconium oxide, silicon dioxide and precipitated and/or pyrogenic silicon dioxide. Of course, the previously cited compounds can be used by themselves or in any combination and also in hydrophilic as well as in hydrophobic form.

Further preferred, the at least one reinforcing filler is present in the form of nanoparticles as fiber or flaky filler, for example, as fibrous mineral filler, or as fibrous synthetic filler.

The proportion of reinforcing filler in the dental material according to the invention is typically 0.1 to 50 percent by weight, preferred, 0.2 to 20 percent by weight and particularly preferred, 0.5 to 10 percent by weight relative to the total dental material.

In principle, the same substances as those used as reinforcing fillers are suitable as non-reinforcing fillers, whereby, however, the non-reinforcing fillers must have a BET surface of less than 50 $m^2/g$ (Journal Series Pigments Degussa Silicon Dioxides, Number 12, Page 5 and Number 13, Page 3). Preferred non-reinforcing fillers are substances that are selected from the group consisting of dental glasses that preferably contain X-ray-opaque ingredients, alkaline earth metal oxides, alkaline earth metal hydroxides, alkaline earth metal fluorides, alkaline earth metal carbonates, calcium apatite $(Ca_5[(F, Cl, OH, \frac{1}{2}CO_3)|(PO_4)_3])$, in particular, calcium hydroxyl apatite $(Ca_5[(OH)|(PO_4)_3])$, titanium dioxide, zirconium oxide, aluminum hydroxide, silicon dioxide (e.g. cristobalite, fused silica) precipitated silicon dioxide and calcium carbonate. Of course, the compounds cited above can be used individually or in any combination, and also in hydrophilic as well as in hydrophobic form.

Preferably, the non-reinforcing fillers used have an average grain size that is larger than 0.1 µm (Ullmann Encyclopedia of Technical Chemistry, volume 21, page 523).

The proportion of non-reinforcing filler in the dental material according to the invention is typically 5 to 80 percent by weight, preferably 10 to 70 percent by weight, and particularly preferred, 20 to 70 percent by weight relative to the total amount of dental material.

Furthermore, larger amounts of the selected X-ray-opaque fillers can also be present in the at least one base paste and/or the at least one catalyst paste. Preferably, this is irregularly shaped or spherical $YbF_3$ or $YF_3$ powder with an average particle size of the primary particles of 40 nm to 1.5 µm and particularly preferred, core-shell combination products consisting of $YF_3$ or $YbF_3$ core and $SiO_2$ shell, whereby very particularly preferred, the $SiO_2$ shell surface is silanized. In particular, such a core-shell combination product has an index of refraction of 1.48 to 1.54, an average grain size of the agglomerated particles between 0.5 and 5 µm, as measured with a laser refraction particle size measurement device SALD-2001 (Schimadzu), and a B.E.T. surface of 2 to 5 $m^2/g$, as measured with a Tristar 3000 device from Micromeritics. Thereby, the index of refraction of the core-shell combination product consisting of $YbF_3$ core and $SiO_2$ shell is between 1.52 and 1.54.

According to the invention, the total share of reinforcing and non-reinforcing fillers in the dental material is generally 30 to 80 percent by weight, preferably 40 to 80 percent by weight, particularly preferred 50 to 75 percent by weight relative to the total amount of dental material.

Preferably, the at least one base component and/or the at least one catalyst component contains one or more additives such as, for example, buffer salts, water collectors, metal collectors, metal complex forming agents, further paste forming agents, tensides, active ingredients, substances that make diagnostics possible, tooth substance-etching and/or adhesively-acting substances such as, for example, MDP (methacryloyl decyl phosphate), fluoridation agents, desensitization agents, adhesive agents, coloring, pigments fluorescent coloring, further initiators or initiator components, stabilizers, polymerization inhibitors, thixotropy additives as well as antibacterial substances.

The weight proportion of the additives relative to the total mass of the at least one base component and/or the at least one catalyst component is generally 0 to 20 percent by weight relative to the total mass of the respective component, preferably 0.0001 to 15 percent by weight and very particularly preferred, 0.001 to 10 percent by weight.

In a preferred embodiment, a phase transfer catalyst of the polymerizable dental material is tetrabutylammonium hydrogen sulfate, tetrahexylammonium hydrogen sulfate, tetramethylammonium hydrogen sulfate, tetraphenylphosphonium chloride, tetrabutylphosphonium chloride, bis-[tetrakis(hydroxymethyl)phosphonium] sulfate, 1,2,3-trimethyl-imidazolium methylsulfate, 1,2,3-trimethylimidazoliumethyl sulfate, 1-ethyl,2, 3-dimethylimidazolium ethylsulfate, cetyltrimethylammonium hydrogen sulfate, (vinylbenzyl)trimethylammonium chloride, tetrabutylammonium chloride, tetrabutylammonium acetate, tetrabutylammonium hexafluorophosphate and/or tetrabutylammonium tetrafluoroborate.

The multi component system of this invention is preferably stored in suitable primary packaging, such as cartridges, compules and two-component syringes, as disclosed, for example in EP 2,190,592 B2, and is proportionated in view of its later use.

In a particularly preferred embodiment the multi component system of the invention comprising a catalyst paste (A) filled in a primary packaging and a base paste (B) filled in a primary packaging exhibits a storage stability at 23° C. of at least 15 months.

Storage stability in this context means that the bonding strength of the cured dental material, which has been prepared by using the stored multi component system, in combination with a dental adhesive to dentin, does not differ significantly from the bonding strength of a cured dental material, which has been prepared by using the same multi component system at the beginning of storage, in combination with the same dental adhesive on dentin. Furthermore, storage stability means a negligible change of the performance of the dental material with regard to the binding kinetics, the rheological properties and the mechanical properties compared with the properties at the beginning of the storage.

A composite comprising dentin, dental adhesive and cured dental material obtained by curing the polymerizable dental material, wherein the composite after 24 h of water storage at 37° C. and after 2,500 thermocycles between 5° C. and 55° C. still exists.

The dental mass according to the invention is often used together with a dental adhesive, in particular, in combination with a prime+bond or an all-in-one adhesive.

Therefore, the invention also relates to a modular system (kit of parts) including the polymerizable dental material described above and a dental adhesive.

The invention also relates to a cured dental material that is obtained by mixing the catalyst paste (A) and the base paste (B) according to the invention, preferably at a ratio of 1:20 to 1:1, and by polymerization of the polymerizable dental material.

The invention also relates to the use of a polymerizable dental material containing one of the catalyst pastes (A) described above and a base paste (B) as described above for producing a core-build-up material, a polymerizable composite cement and/or a bulk fill composite for producing core build-ups, mountings and/or tooth fillings.

Furthermore, the invention relates to the use of a polymerizable dental material containing a catalyst paste (A) as described above and a base paste (B) as described above as core build-up material, as polymerizable composite cement, and/or as bulk fill composite.

Refinements, advantages and possibilities of application of the invention also result from the following description of the execution examples. Thereby, all features described by themselves or in any combination constitute the subject matter of the invention regardless of their summary in the claims or their reference.

EXECUTION EXAMPLES

To produce the 1-step, 1-component light-curing, self-etching and self-adhesive bonding, the ingredients listed in the following tables 1 and 2 are used. All ingredients except water and ethanol were weighed into a beaker and homogenized with a centrifugal mixer (Hauschild DAC 150 FVZ). Subsequently, these were dispersed with a three-roll mill, Exakt 80E. After the dispersion, water and ethanol are added; the material was homogenized again in the centrifugal mixer and refilled into black 10 ml dropping bottles (manufactured by Transcodent).

To produce the dual-hardening core build-up composites and composite cements, the ingredients listed in the following tables 3 through 21 were used.

All ingredients are weighed into a beaker and homogenized in a centrifugal mixer (Hauschild DAC 150 FVZ). Subsequently, the dispersion is performed at room temperature using a three-roll mill (Exakt 80E). Afterward, the pastes are homogenized once more in the centrifugal mixer.

TABLE 1

1-Step, 1-Component Light-Curing Bonding without DHEPT - Corresponds to Bonding I (Production Example I); Based on EP 2 554 154 A1, Comparative Example 2

| Ingredient | Amount [% by weight] |
|---|---|
| BisGMA[7] | 28.85 |
| HEMA[8] | 22.50 |
| GDMA[9] | 4.50 |
| CQ[2] | 1.80 |
| EPD[1] | 0.90 |
| MDP[14] | 9.00 |
| BHT[3] | 0.05 |
| HDK H2000 | 4.50 |
| Water | 13.50 |
| Ethanol | 13.50 |
| BAPO[13] | 0.90 |
| DHEPT[11] | 0.00 |
| Total: | 100.00 |

TABLE 2

1-Step, 1-Component Light-Curing Bonding with DHEPT - Corresponds to Bonding II (Production Example II); Based on EP 2 554 154 A1, Example 5

| Ingredient | Amount [% by weight] |
|---|---|
| BisGMA[7] | 27.05 |
| HEMA[8] | 22.50 |
| GDMA[9] | 4.50 |
| CQ[2] | 1.80 |
| EPD[1] | 0.90 |
| MDP[14] | 9.00 |
| BHT[3] | 0.05 |
| HDK H2000 | 4.50 |
| Water | 13.50 |
| Ethanol | 13.50 |
| BAPO[13] | 0.90 |
| DHEPT[11] | 1.80 |
| Total: | 100.00 |

TABLE 3

Polymerizable Dental Material Catalyst Paste (Production Example 1)

| Ingredient | Amount [% by weight] |
|---|---|
| UDMA[4] | 24.75 |
| DDDDMA[5] | 6.25 |
| TMPTMA[6] | 2.00 |
| HDK H2000 | 4.50 |
| YbF$_3$ (100 nm) | 20.00 |
| Cristobalite powder (6 μm with methacrylate silane) | 41.61 |
| BPO[10] | 0.80 |
| BHT[3] | 0.09 |
| Total: | 100.00 |

TABLE 4

Polymerizable Dental Material Base Paste (Production Example 2)

| Ingredient | Amount [% by weight] |
|---|---|
| UDMA[4] | 24.75 |
| DDDDMA[5] | 6.25 |
| TMPTMA[6] | 2.00 |
| HDK H2000 | 4.50 |
| YbF$_3$ (100 nm) | 20.00 |
| Cristobalite powder (6 μm with methacrylate silane) | 41.10 |
| DHEPT[11] | 0.90 |
| EPD[1] | 0.20 |
| CQ[2] | 0.09 |
| BHT[3] | 0.01 |
| HMBP[12] | 0.20 |
| Total: | 100.00 |

TABLE 5

Polymerizable Dental Material Base Paste (Production Example 3)

| Ingredient | Amount [% by weight] |
|---|---|
| UDMA[4] | 24.75 |
| DDDDMA[5] | 6.25 |
| TMPTMA[6] | 2.00 |
| HDK H2000 | 4.50 |
| YbF$_3$ (100 nm) | 20.00 |
| Cristobalite powder (6 μm with methacrylate silane) | 39.10 |
| DHEPT[11] | 0.90 |
| EPD[1] | 0.20 |
| CQ[2] | 0.09 |
| Sodium sulfite (5 μm) | 2.00 |
| BHT[3] | 0.01 |
| HMBP[12] | 0.20 |
| Total: | 100.00 |

TABLE 6

Polymerizable Dental Material Catalyst
Paste (Production Example 4)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.93 |
| BPO[10] | 0.80 |
| BHT[3] | 0.09 |
| Tetraethylammonium ptoluenesulfonate (phase transfer catalyst not according to the invention) | 0.18 |
| Total: | 100.00 |

TABLE 7

Polymerizable Dental Material Catalyst
Paste (Production Example 5)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.91 |
| BPO[10] | 0.80 |
| BHT[3] | 0.09 |
| Tetrabutylammonium chloride (phase transfer catalyst according to the invention) | 0.20 |
| Total: | 100.00 |

TABLE 8

Polymerizable Dental Material Catalyst
Paste (Production Example 6)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm mit methacrylate silane) | 43.91 |
| BPO[10] | 0.80 |
| BHT[3] | 0.09 |
| (Vinylbenzyl)trimethylammonium chloride (phase transfer catalyst according to the invention) | 0.20 |
| Total: | 100.00 |

TABLE 9

Polymerizable Dental Material Catalyst
Paste (Production Example 7)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.91 |
| BPO[10] | 0.80 |
| BHT[3] | 0.09 |
| Tetrabutylammonium hydrogen sulfate (phase transfer catalyst according to the invention) | 0.20 |
| Total: | 100.00 |

TABLE 10

Polymerizable Dental Material Catalyst
Paste (Production Example 8)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 44.01 |
| BPO[10] | 0.80 |
| BHT[3] | 0.09 |
| Tetrabutylammonium hydrogen sulfate (phase transfer catalyst according to the invention) | 0.10 |
| Total: | 100.00 |

TABLE 11

Polymerizable Dental Material Catalyst
Paste (Production Example 9)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.71 |
| BPO[10] | 0.80 |
| BHT[3] | 0.09 |
| Tetrabutylammonium hydrogen sulfate (phase transfer catalyst according to the invention) | 0.40 |
| Total: | 100.00 |

TABLE 12

Polymerizable Dental Material Catalyst
Paste (Production Example 10)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 44.01 |

TABLE 12-continued

Polymerizable Dental Material Catalyst Paste (Production Example 10)

| Ingredient | Amount [% by weight] |
|---|---|
| BPO[10] | 0.80 |
| BHT[3] | 0.09 |
| Tetramethylammonium hydrogen sulfate (phase transfer catalyst according to the invention) | 0.10 |
| Total: | 100.00 |

TABLE 13

Polymerizable Dental Material Catalyst Paste (Production Example 11)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.84 |
| BPO[10] | 0.80 |
| BHT[3] | 0.09 |
| Tetrahexylammonium hydrogen sulfate (phase transfer catalyst according to the invention) | 0.27 |
| Total: | 100.00 |

TABLE 14

Polymerizable Dental Material Catalyst Paste (Production Example 12)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.88 |
| BPO[10] | 0.80 |
| BHT[3] | 0.09 |
| Cetyltrimethylammonium hydrogen sulfate (phase transfer catalyst according to the invention) | 0.23 |
| Total: | 100.00 |

TABLE 15

Polymerizable Dental Material Catalyst Paste (Production Example 13)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.93 |
| BPO[10] | 0.80 |
| BHT[3] | 0.09 |
| Tetrabutylammonium acetate (phase transfer catalyst according to the invention) | 0.18 |
| Total: | 100.00 |

TABLE 16

Polymerizable Dental Material Catalyst Paste (Production Example 14)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.91 |
| BPO[10] | 0.80 |
| BHT[3] | 0.09 |
| Tetrabutylammonium tetrafluoroborate (phase transfer catalyst according to the invention) | 0.20 |
| Total: | 100.00 |

TABLE 17

Polymerizable Dental Material Catalyst Paste (Production Example 15)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.88 |
| BPO[10] | 0.80 |
| BHT[3] | 0.09 |
| Tetrabutylammonium hexafluorophosphate (phase transfer catalyst according to the invention) | 0.23 |
| Total: | 100.00 |

TABLE 18

Polymerizable Dental Material Catalyst Paste (Production Example 16)

| Ingredient | Amount [% by weight] |
|---|---|
| UDMA[4] | 24.75 |
| DDDDMA[5] | 6.25 |
| TMPTMA[6] | 2.00 |
| HDK H2000 | 2.00 |
| YbF$_3$ (100 nm) | 20.00 |
| Cristobalite powder (6 μm with methacrylate silane) | 43.91 |

TABLE 18-continued

Polymerizable Dental Material Catalyst Paste (Production Example 16)

| Ingredient | Amount [% by weight] |
|---|---|
| BPO[10) | 0.80 |
| BHT[3) | 0.09 |
| 1-Ethyl-2,3-dimethyl imidazoliumethylsulfate (phase transfer catalyst according to the invention) | 0.20 |
| Total: | 100.00 |

TABLE 19

Polymerizable Dental Material Catalyst Paste (Production Example 17)

| Ingredient | Amount [% by weight] |
|---|---|
| UDMA[4) | 24.75 |
| DDDDMA[5) | 6.25 |
| TMPTMA[6) | 2.00 |
| HDK H2000 | 2.00 |
| YbF$_3$ (100 nm) | 20.00 |
| Cristobalite powder (6 μm with methacrylate silane) | 43.87 |
| BPO[10) | 0.80 |
| BHT[3) | 0.09 |
| Bis[tetrakis(hydroxymethyl)phosphonium]sulfate (phase transfer catalyst according to the invention) | 0.24 |
| Total: | 100.00 |

TABLE 20

Polymerizable Dental Material Catalyst Paste (Production Example 18)

| Ingredient | Amount [% by weight] |
|---|---|
| UDMA[4) | 24.75 |
| DDDDMA[5) | 6.25 |

TABLE 20-continued

Polymerizable Dental Material Catalyst Paste (Production Example 18)

| Ingredient | Amount [% by weight] |
|---|---|
| TMPTMA[6) | 2.00 |
| HDK H2000 | 2.00 |
| YbF$_3$ (100 nm) | 20.00 |
| Cristobalite powder (6 μm with methacrylate silane) | 43.89 |
| BPO[10) | 0.80 |
| BHT[3) | 0.09 |
| Tetraphenylphosphonium chloride (phase transfer catalyst according to the invention) | 0.22 |
| Total: | 100.00 |

TABLE 21

Polymerizable Dental Material Catalyst Paste (Production Example 19)

| Ingredient | Amount [% by weight] |
|---|---|
| UDMA[4) | 24.75 |
| DDDDMA[5) | 6.25 |
| TMPTMA[6) | 2.00 |
| HDK H2000 | 2.00 |
| YbF$_3$ (100 nm) | 20.00 |
| Cristobalite powder (6 μm with methacrylate silane) | 43.88 |
| BPO[10) | 0.80 |
| BHT[3) | 0.09 |
| (4-Methylthiophenyl)methyl phenyl sulfonium triflate (phase transfer catalyst according to the invention) | 0.23 |
| Total: | 100.00 |

[1) EPD is ethyl-4-dimethylaminobenzoate.
[2) CQ is DL-camphorquinone.
[3) BHT is 2,6-di-tert-butyl-4-methylphenol.
[4) UDMA is an isomer mixture consisting of di-2-methacryloxyethyl-2,2,4-trimethyl hexamethylene dicarbamate and di-2-(meth)acryl-oxyethyl-2,4,4-trimethyl-hexamethylene dicarbamate corresponding to Formula (I).

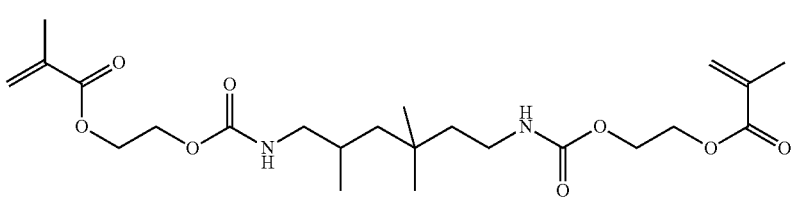

(I)

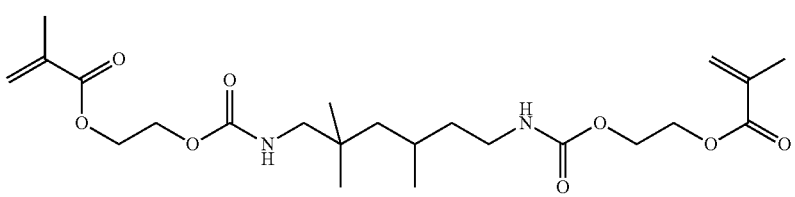

UDMA

5) DDDDMA is 1,12-dodecanediol dimethacrylate.
6) TMPTMA is trimethylolpropane trimethacrylate.
7) BisGMA is bisphenol-A-glycidyl methacrylate.
8) HEMA is 2-hydoxyethyl methacrylate.
9) GDMA is glycerin-1,3-dimethacrylate.
10) BPO is dibenzoyl peroxide.
11) DHEPT is p-tolyl-diethanol amine.
12) HMBP is 2-hydroxy-4-methoxy-benzophenone.
13) BAPO is bis(2,4,6-trimethylbenzoyl)phenylphosphine oxide, that functions as auxiliary initiator for light-curing.
14) MDP is 10-methacryloyloxdecyl dihydrogen phosphate.

To produce the patent and comparative examples, the catalyst paste and the base paste formulations were filled into 5 ml double syringes of the type Mixpac 1:1 SDL X05-01-52 (Sulzer), corresponding to the combinations listed in Table 19. For testing, the dental masses were discharged through a root canal-tip of the type IOR 209-20, via a static mixer of the type Mixpac MLT 2.5-10-D (Sulzer).

TABLE 22

Combination of the Production Examples

| Catalyst Paste | Base Paste | Combination |
| --- | --- | --- |
| Production Example 1 | Production Example 2 | Comparative Example 1 |
| Production Example 1 | Production Example 3 | Comparative Example 2 |
| Production Example 4 | Production Example 3 | Comparative Example 3 |
| Production Example 5 | Production Example 3 | Patent Example 1 |
| Production Example 6 | Production Example 3 | Patent Example 2 |
| Production Example 7 | Production Example 3 | Patent Example 3 |
| Production Example 8 | Production Example 3 | Patent Example 4 |
| Production Example 9 | Production Example 3 | Patent Example 5 |
| Production Example 10 | Production Example 3 | Patent Example 6 |
| Production Example 11 | Production Example 3 | Patent Example 7 |
| Production Example 12 | Production Example 3 | Patent Example 8 |
| Production Example 13 | Production Example 3 | Patent Example 9 |
| Production Example 14 | Production Example 3 | Patent Example 10 |
| Production Example 15 | Production Example 3 | Patent Example 11 |
| Production Example 16 | Production Example 3 | Patent Example 12 |
| Production Example 17 | Production Example 3 | Patent Example 13 |
| Production Example 18 | Production Example 3 | Patent Example 14 |
| Production Example 19 | Production Example 3 | Patent Example 15 |

To test the bonding strength, the core build-up materials in Comparative Examples 1 through 3 and Patent Examples 1 through 15, and the comparative material LuxaCore Smartmix Dual (DMG, LOT 707376) were combined with Bonding I and II. The experiments were performed using human dentin based on the ISO 29022 standard.

For this purpose, human teeth were embedded in cold-mounting materials (VariKwick, manufactured by Bühler) and the dentin was exposed by grinding the surface. The bonding was applied to the test specimens treated in this way and 10 s light-cured (Superlite 1100, made by M+W Dental). Subsequently, the test specimens were inserted into a bonding clamp (Bonding Clamp, manufactured by Ultradent), that contains a plug-in mold for the core build-up cylinder to be attached (Bonding Mold Insert, manufactured by Ultradent). The fill cavity in the mold was positioned in the center of the tooth at a location suitable for the composite and lowered. Next, the core build-up material was applied to the composite surface and stored in the dark for seven minutes at 37° C. in self-curing mode. Upon the elapse of this time, the test specimens were removed from the mold and placed in water for another 24 hours at 37° C.

Upon the elapse of this time, a shearing test was performed using a universal testing machine (Zwicki Universal Testing Machine Z0.5 TN) with a corresponding set-up. To do so, the composite test specimens were clamped into a test clamp (Test Base Clamp, manufactured by Ultradent). In the clamp, the test specimens were aligned abutting at the tooth under a cross head with recessed blade (Crosshead Assembly, manufactured by Ultradent) in the center of the composite cylinder. The test specimens were stress-tested up to breaking at a testing speed of 1.0 mm/min. The results are shown in Table 23.

TABLE 23

Results

| Polymerizable Dental Material | Adhesive | Bonding Strength at Dentin* [MPa] |
| --- | --- | --- |
| Examples Not According to the Invention: | | |
| LuxaCore Smartmix Dual LOT 707376 white | Production Example I: Bonding I | 7.6 |
| LuxaCore Smartmix Dual LOT 707376 white | Production Example II: Bonding II | 3.9 |
| Comparative Example 1: Polymerizable Dental Material | Production Example I: Bonding I | 7.3 |
| Comparative Example 1: Polymerizable Dental Material | Production Example II: Bonding II | 3.8 |
| Comparative Example 2: Polymerizable Dental Material - contains Sodium Sulfite (15.87 mmol) | Production Example I: Bonding I | 8.3 |
| Comparative Example 2: Polymerizable Dental Material - contains Sodium Sulfite (15.87 mmol) | Production Example II: Bonding II | 9.5 |
| Comparative Example 3: Polymerizable Dental Material - contains Sodium Sulfite (15.87 mmol) and Tetraethylammonium p-toluenesulfonate (0.59 mmol; Phase Transfer Catalyst) | Production Example I: Bonding I | 8.6 |
| Examples According to the Invention Using Ammonium Salts as Phase Transfer Catalysts: | | |
| Patent Example 1: Polymerizable Dental Material - contains Sodium Sulfite (15.87 mmol) and Tetrabutylammonium Chloride (0.72 mmol; Phase Transfer Catalyst) | Production Example I: Bonding I | 18.3 |
| Patent Example 2: Polymerizable Dental Material - contains Sodium Sulfite (15.87 mmol) and (Vinylbenzyl)trimethylammonium Chloride (0.94 mmol; Phase Transfer Catalyst) | Production Example I: Bonding I | 12.8 |
| Patent Example 3: Polymerizable Dental Material - contains Sodium Sulfite (15.87 mmol) and Tetrabutylammonium Hydrogen Sulfate (0.59 mmol; Phase Transfer Catalyst) | Production Example I: Bonding I | 15.3 |

TABLE 23-continued

Results

| Polymerizable Dental Material | Adhesive | Bonding Strength at Dentin* [MPa] |
|---|---|---|
| Patent Example 3: Polymerizable Dental Material - contains Sodium Sulfite (15.87 mmol) and Tetrabutylammonium Hydrogen Sulfate (0.59 mmol; Phase Transfer Catalyst) After 15 Months Storage at 23 ± 1° C. | Production Example I: Bonding I | 15.7 |
| Patent Example 3: Polymerizable Dental Material - contains Sodium Sulfite (15.87 mmol) and Tetrabutylammonium Hydrogen Sulfate (0.59 mmol; Phase Transfer Catalyst) | Production Example II: Bonding II | 14.6 |
| Patent Example 3: Polymerizable Dental Material - contains Sodium Sulfite (15.87 mmol) and Tetrabutylammonium Hydrogen Sulfate (0.30 mmol; Phase Transfer Catalyst) | Production Example I: Bonding I | 13.3 |
| Patent Example 3: Polymerizable Dental Material - contains Sodium Sulfite (15.87 mmol) and Tetrabutylammonium Hydrogen Sulfate (1.18 mmol; Phase Transfer Catalyst) | Production Example I: Bonding I | 15.8 |
| Patent Example 6: Polymerizable Dental Material - contains Sodium Sulfite (15.87 mmol) and Tetramethylammonium Hydrogen Sulfate (0.59 mmol; Phase Transfer Catalyst) | Production Example I: Bonding I | 14.5 |
| Patent Example 7: Polymerizable Dental Material - contains Sodium Sulfite (15.87 mmol) and Tetrahexylammonium Hydrogen Sulfate (0.59 mmol; Phase Transfer Catalyst) | Production Example I: Bonding I | 13.4 |
| Patent Example 8: Polymerizable Dental Material - contains Sodium Sulfite (15.87 mmol) and Cetyltrimethylammonium Hydrogen Sulfate (0.59 mmol; Phase Transfer Catalyst) | Production Example I: Bonding I | 12.8 |
| Patent Example 9: Polymerizable Dental Material - contains Sodium Sulfite (15.87 mmol) and Tetrabutylammonium Acetate (0.59 mmol; Phase Transfer Catalyst) | Production Example I: Bonding I | 13.0 |
| Patent Example 10: Polymerizable Dental Material - contains Sodium Sulfite (15.87 mmol) and Tetrabutylammonium Tetrafluoroborate (0.61 mmol; Phase Transfer Catalyst) | Production Example I: Bonding I | 14.4 |
| Patent Example 11: Polymerizable Dental Material - contains Sodium Sulfite (15.87 mmol) and Tetrabutylammonium Hexafluorophosphate (0.59 mmol; Phase Transfer Catalyst) | Production Example I: Bonding I | 10.5 |
| Examples According to the Invention Using Heterocyclic Ammonium Salt as Phase Transfer Catalyst: | | |
| Patent Example 12: Polymerizable Dental Material - contains Sodium Sulfite (15.87 mmol) and 1-Ethyl-2,3-dimethyl-imidazoliumethyl Sulfate (0.8 mmol; Phase Transfer Catalyst) | Production Example I: Bonding I | 11.2 |
| Examples According to the Invention Using Phosphonium Salts as Phase Transfer Catalysts: | | |
| Patent Example 13: Polymerizable Dental Material - contains Sodium Sulfite (15.87 mmol) and Bis[tetrakis(hydroxymethyl)phosphonium]sulfate (0.59 mmol; Phase Transfer Catalyst) | Production Example I: Bonding I | 11.7 |
| Patent Example 14: Polymerizable Dental Material - contains Sodium Sulfite (15.87 mmol) and Tetraphenylphosphonium Chloride (0.59 mmol; Phase Transfer Catalyst) | Production Example I: Bonding I | 10.5 |
| Examples According to the Invention Using Sulfonium Salts as Phase Transfer Catalysts: | | |
| Patent Example 15: Polymerizable Dental Material - contains Sodium Sulfite (15.87 mmol) and (4-Methylthiophenyl)methyl Phenyl Sulfonium Triflate (0.59 mmol; Phase Transfer Catalyst) | Production Example I: Bonding I | 14.0 |
| Example According to the Invention Using Various Commercial All-in-One Adhesives: | | |
| Patent Example 3: Polymerizable Dental Material - contains Sodium Sulfite (15.87 mmol) and Tetrabutylammonium Hydrogen Sulfate (0.59 mmol; Phase Transfer Catalyst) | Clearfil S3 Bond Plus (Kuraray) | 19.5 |
| Patent Example 3: Polymerizable Dental Material - contains Sodium Sulfite (15.87 mmol) and Tetrabutylammonium Hydrogen Sulfate (0.59 mmol; Phase Transfer Catalyst) | Clearfil Universal Bond (Kuraray) | 14.9 |
| Patent Example 3: Polymerizable Dental Material - contains Sodium Sulfite (15.87 mmol) and Tetrabutylammonium Hydrogen Sulfate (0.59 mmol; Phase Transfer Catalyst) | Scotchbond Universal (3M Espe) | 16.2 |
| Patent Example 3: Polymerizable Dental Material - contains Sodium Sulfite (15.87 mmol) and Tetrabutylammonium Hydrogen Sulfate (0.59 mmol; Phase Transfer Catalyst) | Xeno Select (Dentsply) | 11.6 |
| Patent Example 3: Polymerizable Dental Material - contains Sodium Sulfite (15.87 mmol) and Tetrabutylammonium Hydrogen Sulfate (0.59 mmol; Phase Transfer Catalyst) | All Bond Universal (Bisco) | 11.0 |
| Patent Example 3: Polymerizable Dental Material - contains Sodium Sulfite (15.87 mmol) and Tetrabutylammonium Hydrogen Sulfate (0.59 mmol; Phase Transfer Catalyst) | iBond Universal (Heraeus Kulzer) | 10.1 |

*The number of non-adhering test specimens was included at a value of zero.

Table 23 shows the following findings:

The commercially available and in Germany, the leading core build-up material "LuxaCore Smartmix Dual" exhibits a low bonding strength with both bonding variants (Bonding I, according to EP 2 554 154 A1, Comparative Example 2, page 19; Bonding II, according to EP 2 554 154 A1, Example 5, page 31). Hereby, the bonding strength with Bonding II is once again significantly lower than in the case of Bonding I, which can be explained thereby, that in Bonding II, some of the etching effect of the phosphoric acid methacrylate is neutralized by the aromatic amine DHEPT it also contains.

The polymerizable dental material described in Comparative Example 1 (initiator composition without the water-soluble reduction agent comparable with Comparative Example 3, page 28, of EP 2 554 154 A1) exhibits a low bonding strength with both bonding variants, completely analogous to "Luxacore Smartmix Dual". Here as well, the bonding strength with Bonding II is once again significantly lower compared to that with Bonding I. This shows that the composition with respect to the monomers and fillers relative to the bonding strength that was used in all examples is comparable with other commercially available core build-up materials.

The polymerizable dental material described in Comparative Example 2 (initiator composition with the water-soluble reduction agent comparable with Example 5, page 17, of EP 2 554 154 A1) shows, in particular, in connection with Bonding II, a significantly higher bonding strength compared with the polymerizable dental material in Comparative Example 1. In this case, the bonding strength with Bonding I is significantly lower than with Bonding II. This leads to two conclusions: a) The use of a water-soluble reducing compound in the curable dental material does not lead to the desired success for hydrophobic compositions that are suitable for core build-up materials, in contrast to the hydrophilic bonding agents of EP 1 780 223 B1 b) If Bonding II is used with a reducing amine according to the invention in EP 2 554 154 A1, the use of a water-soluble reducing compound in the curable composition of the composite improves the bonding strength significantly. This confirms the invention disclosed in EP 2 554 154 A1 with a special adhesive containing an amine as reduction agent. However, the advantage over prior art that was presented there is clearly achieved only by using the special adhesive contained in the kit.

The polymerizable dental material described in Comparative Example 3 (contains the phase transfer catalyst tetraethylammonium p-toluene sulfonate—not according to the invention) shows a comparable bonding strength to that of Bonding I with the composition of Comparative Example 2, in which no phase transfer catalyst was used. This confirms that phase transfer catalysts with relatively hydrophobic anions having more than 4 C atoms are ineffective.

The polymerizable dental materials described in Patent Examples 1 through 15 exhibit a high degree of bonding strength with Bonding I that is more than 10 MPa. This confirms that by using the phase transfer catalysts according to the invention, the bonding strength can be improved significantly, whereby ammonium cations with different substituents, different anions with no more than 4 C-atoms and different concentrations of the phase transfer catalyst can be used. Further, phase transfer catalysts based on ammonium salts, as well as those based on heterocyclic ammonium derivatives are suitable, such the imidazolium derivative used in Patent Example 12, the phase transfer catalysts based on phosphonium salts (Patent Example 13 and 14) and also the phase transfer catalysts based on sulfonium salts (Patent Example 15). The applied polymerizable dental materials showed a good shelf life. Storage over 15 months did not result in a reduction of the bonding strength. With Bonding II according to the invention disclosed in EP 2 554 154 A1—as is shown with the core build-up material in Patent Example 3—the bonding strength cannot be improved any further, i.e. using a special adhesive that contains an amine as reduction agent is therefore not required in the curable composite when using a phase transfer catalyst according to this patent specification.

The polymerizable dental material in Patent Example 3 was also tested with several commercially available light-curing, all-in-one adhesives from various manufacturers. It was possible to achieve a high degree of bonding strength in each case.

Additionally, micro-tensile tests were conducted using commercially available core build-up materials in combination with various commercially available adhesives.

For this test, 300 intact, non-carious, unrestored human third molars were stored in an aqueous solution of 0.5% chloramine T at 4° C. for up to 30 days. The teeth were debrided of residual plaque and calculus, and examined under a light microscope at 20× magnification to ensure that they were free of defects. Standardized Class I cavity preparations (4 mm in width and length, 4 mm in depth) were performed. Cavities were cut using coarse diamond burs under profuse water cooling (80 µm, Two-Striper Prep-Set, Premier, St. Paul, USA), and finished with a 25 µm finishing diamond. Inner angles of the cavities were rounded and the margins were not bevelled. To guarantee a rectangular relation between the bonded interface and the direction of the later cut µ-TBS beam, the cusps were flattened 2 mm and then the cavity floor was prepared parallel to the flattened cusps.

Cavities were overfilled 5 mm in bulk with different adhesives and core build-up materials under elevated room temperature (30° C. for simulation of intraoral temperature). Adhesives (separately cured according to the instructions of the manufacturers) and build-up resin composite were polymerized with a Bluephase light-curing unit (Ivoclar Vivadent) in accordance to the manufacturers' recommendations. The intensity of the light was checked periodically with a radiometer (Demetron Research Corp, Danbury, Conn., USA) to ensure that 1200 mW/cm$^2$ was always exceeded during the experiments.

After 24 h of water storage at 37° C. and 2,500 thermocycles (5° C./55° C.), the peripheral areas of the reconstructed/filled teeth were removed, remaining specimens were sectioned into slices in apical direction, which were sectioned again to receive resin-dentin beams. The saw was adjusted to steps of 1 mm, due to the thickness of the blade (300 µm) resulting in sticks with a cross-sectional area of 700×700 µm (0.5 mm$^2$). From the resulting sticks of each group, 20 were selected (n=20). These 20 sticks had to have a remaining dentin thickness to the pulp of 2.0±0.5 mm. If more than 20 beams were collected with the correct remaining dentin thickness, 20 sticks were randomly selected. For the case that one or more of the selected sticks failed due to the sectioning process, the percentage of prematurely failed specimens in relation to the total number of selected specimens was recorded. The same (or approximated) percentage of the 20 final specimens received 0 MPa as final µ-TBS result. The µ-TBS sticks were stored in distilled water for 24 hours at 37° C. and then fractured according to a well-suited protocol, following: Frankenberger R, Pashley D H, Reich S M, Lohbauer U, Petschelt A, Tay F R. Characterisation of resin-dentine interfaces by compressive cyclic loading. Biomaterials 2005; 26:2043-2052.

The following table shows the bonding strengths in MPa for core build-up materials using various combinations of adhesives.

| Core Build-up Material | Adhesive | Bonding Strength (MPa) |
| --- | --- | --- |
| According to Patent Example 3 | Adhese ® Universal | 5.2 |
| According to Patent Example 3 | All-Bond Universal ® | 7.4 |
| According to Patent Example 3 | Clearfill ® S$^3$ Bond Plus | 20.3 |
| According to Patent Example 3 | Clearfill ® SE Bond | 21.3 |
| According to Patent Example 3 | Futurabond ® U | 5.2 |
| According to Patent Example 3 | i-Bond ® | 5.5 |
| According to Patent Example 3 | Scotchbond ® Universal | 9.4 |
| According to Patent Example 3 | Xeno ® Select | 11.2 |
| MultiCore ® Flow | Adhese ® Universal | 0 |
| MultiCore ® Flow | All-Bond Universal ® | 0 |
| MultiCore ® Flow | Clearfill ® S$^3$ Bond Plus | 0 |
| MultiCore ® Flow | Clearfill ® SE Bond | 0 |
| MultiCore ® Flow | Futurabond ® U | 0 |
| MultiCore ® Flow | i-Bond ® | 0 |
| MultiCore ® Flow | Scotchbond ® Universal | 0 |
| MultiCore ® Flow | Xeno ® Select | 0 |
| Rebilda DC | Adhese ® Universal | 0 |
| Rebilda DC | All-Bond Universal ® | 0 |
| Rebilda DC | Clearfill ® S$^3$ Bond Plus | 0 |

-continued

| Core Build-up Material | Adhesive | Bonding Strength (MPa) |
|---|---|---|
| Rebilda DC | Clearfill ® SE Bond | 0 |
| Rebilda DC | Futurabond ® U | 0 |
| Rebilda DC | i-Bond ® | 0 |
| Rebilda DC | Scotchbond ® Universal | 0 |
| Rebilda DC | Xeno ® Select | 0 |
| LuxaCore Dual | Adhese ® Universal | 0 |
| LuxaCore Dual | All-Bond Universal ® | 0 |
| LuxaCore Dual | Clearfill ® S³ Bond Plus | 0 |
| LuxaCore Dual | Clearfill ® SE Bond | 0 |
| LuxaCore Dual | Futurabond ® U | 0 |
| LuxaCore Dual | i-Bond ® | 0 |
| LuxaCore Dual | Scotchbond ® Universal | 0 |
| LuxaCore Dual | Xeno ® Select | 0 |
| Core Paste ® XP | Adhese ® Universal | 0 |
| Core Paste ® XP | All-Bond Universal ® | 0 |
| Core Paste ® XP | Clearfill ® S³ Bond Plus | 0 |
| Core Paste ® XP | Clearfill ® SE Bond | 0 |
| Core Paste ® XP | Futurabond ® U | 0 |
| Core Paste ® XP | i-Bond ® | 0 |
| Core Paste ® XP | Scotchbond ® Universal | 0 |
| Core Paste ® XP | Xeno ® Select | 0 |

What is claimed is:

1. A two-part dental material, containing a catalyst paste (A) and a base paste (B) separate from the catalyst paste (A),
wherein the catalyst paste (A) contains at least one organic peroxygen compound, at least one radically polymerizable organic (meth)acrylic monomer selected from the group consisting of 2-hydroxyethylmethacrylate, di- and higher acrylates, di- and higher acrylamides, di- and higher methacrylates and di- and higher methacrylamides, and at least one filler, and wherein the base paste (B) contains at least one radically polymerizable organic (meth)acrylic monomer, an amine as co-initiator of the radical polymerization, at least one filler, and at least one salt-like, water-soluble and powdery reduction agent that is dispersed therein, and
wherein only the catalyst paste (A) contains at least one phase transfer catalyst that is selected from the group consisting of ammonium, phosphonium, and/or sulfonium salts that contain an inorganic or organic anion, provided that the phase transfer catalyst—in the case of organic anions—contains only those having 1-4 carbon atoms, and that the anions of sulfinic acids are precluded.

2. The two-part dental material as recited in claim 1, wherein the at least one, salt-like, water-soluble and powdery reduction agent is selected from the group consisting of sulfites.

3. The two-part dental material as recited in claim 1, wherein the proportion of the at least one phase transfer catalyst is 0.01 to 5 percent by weight relative to the total mass of the catalyst paste (A).

4. The two-part dental material as recited in claim 1, wherein the co-initiator of the radical polymerization is a primary, secondary, or tertiary amine.

5. The two-part dental material as recited in claim 1, wherein such is dual-hardening and that additionally, at least one photoinitiator is provided in the catalyst paste (A) and/or in the base paste (B).

6. The two-part dental material as recited in claim 1, wherein the at least one radically polymerizable organic (meth)acrylic monomer is selected from the group consisting of the di and higher acrylates, di and higher acrylamides, di and higher methacrylates and di and higher methacrylamides.

7. The two-part dental material as recited in claim 1, wherein the at least one radically polymerizable organic (meth)acrylic monomer is selected from the group consisting of acrylates or methacrylates containing aromatic groups, acrylates or methacrylates containing aliphatic groups, acrylates or methacrylates containing polyether groups, acrylates or methacrylates containing polyester groups, acrylates or methacrylates containing polyurethane, or combinations of two or more of these monomers.

8. The two-part dental material as recited in claim 7, wherein the at least one radically polymerizable organic (meth)acrylic monomer is selected from the group of monomers consisting of Bisphenol A diacrylate, Bisphenol A dimethacrylate, bisphenol glycidyl acrylate, bisphenol glycidyl methacrylate (Bis-GMA), ethoxylated Bisphenol A diacrylate, ethoxylated Bisphenol A dimethacrylate, 1,6-bis(acryloxy-2-ethoxycarbonylamino)-2,4,4-trimethyl-hexane, 1,6-bis(methacryloxy-2-ethoxy-carbonylamino)-2,4,4-trimethyl-hexane (UDMA), trimethylolpropane triacrylate trimethylolpropane trimethacrylate (TMPTMA), 2-hydroxyethylacrylate, 2-hydroxyethyl methacrylate (HEMA), glycerin-1,3-acrylate, glycerin-1,3-dimethacrylate (GDMA), dodecanediol diacrylate, dodecanediol dimethacrylate, triethylene glycol diacrylate, triethylene glycol dimethacrylate, tetraethylene diacrylate, tetraethylene glycol dimethacrylate or combinations of two or more of these monomers.

9. The two-part dental material as recited in claim 1, wherein the radically polymerizable organic (meth)acrylic monomers are free of any structural units having bisphenol A residues.

10. The two-part dental material as recited in-claim 1, wherein the organic peroxygen compound is selected from the group consisting of organic peroxides.

11. The two-part dental material as recited in claim 1, wherein the anion of the phase transfer catalyst is selected from the group consisting of halogenides, hydroxides, anions of inorganic acids, pseudo halogenide anions or halogen complexes of aluminate, silicate or phosphate, or anions of organic acids having 1-4 carbon atoms, excluding anions of sulfinic acids.

12. The two-part dental material as recited in claim 11, wherein the anion of the phase transfer catalyst is selected from the group consisting of fluoride, chloride, bromide, iodide, hydroxide, sulfate, hydrogen sulfate, dihydrogen sulfate, phosphate, phosphonate, borate, chlorate, perchlorate, nitrite, nitrate, hydrogen carbonate, carbonate, tetrafluoroborate, tetrachloroaluminate, hexafluorosilicate, hexachlorophosphate, formate, acetate, butyrate, fumarate, maleate, glutarate, lactate, malate, malonate, oxalate, pyruvate or tartrate.

13. The two-part dental material as recited in claim 1, wherein the phase transfer catalyst is an ammonium salt having the cation $NR_1R_2R_3R_4$, wherein $R_1$, $R_2$, $R_3$ and $R_4$—independent of each other—mean $C_1$ to $C_{20}$ alkyl, $C_1$ to $C_{20}$ alkyl halogenide, $C_1$ to $C_{20}$ alkyloxy, $C_1$ to $C_{20}$ hydroxyalkyl, $C_2$ to $C_{20}$ alkenyl, $C_2$ to $C_{20}$ alkenyloxy, $C_2$ to $C_{20}$ alkinyl, $C_2$ to $C_{20}$ alkinyloxy, $C_2$ to $C_{20}$ alkyl ester, aryl, aryloxy, aralkyl, aralkyloxy, alkylaryl and/or alkylaryloxy.

14. The two-part dental material as recited in claim 1, wherein the phase transfer catalyst is a phosphonium salt having the cation $PR_1R_2R_3R_4$, wherein $R_1$, $R_2$, $R_3$ and $R_4$—independent of each other—mean $C_1$ to $C_{20}$ alkyl, $C_1$ to $C_{20}$ alkyl halogenide, $C_1$ to $C_{20}$ alkyloxy, $C_2$ to $C_{20}$ alkenyl, $C_2$ to $C_{20}$ alkenyloxy, $C_2$ to $C_{20}$ alkinyl, $C_2$ to $C_{20}$ alkinyloxy, $C_2$ to $C_{20}$ alkyl ester, aryl, aryloxy, aralkyl, aralkyloxy, alkylaryl and/or alkylaryloxy.

15. The two-part dental material as recited in claim 1, wherein the phase transfer catalyst is a sulfonium salt having the cation $SR_1R_2R_3$, wherein $R_1$, $R_2$ und $R_3$—independent of each other—mean $C_1$ to $C_{20}$ alkyl, $C_1$ to $C_{20}$ alkyl halogenide, $C_1$ to $C_{20}$ alkyloxy, $C_2$ to $C_{20}$ alkenyl, $C_2$ to $C_{20}$ alkenyloxy, $C_2$ to $C_{20}$ alkinyl, $C_2$ to $C_{20}$ alkinyloxy, $C_2$ to $C_{20}$ alkyl ester, aryl, aryloxy, aralkyl, aralkyloxy, alkylaryl and/or alkylaryloxy.

16. The two-part dental material as recited in claim 1, wherein the phase transfer catalyst is tetrabutylammonium hydrogen sulfate, tetramethylammonium hydrogen sulfate, tetrahexylammonium hydrogen sulfate, bis[tetrakis(hydroxymethyl)-phosphonium] sulfate, tetraphenylphosphonium chloride, 1-ethyl-2,3-dimethylimidazoliumimidazolium ethylsulfate, cetyltrimethylammonium hydrogen sulfate, (vinylbenzyl) trimethylammonium chloride, tetrabutylammonium chloride and/or tetrabutylammonium tetrafluoroborate.

17. A cured dental material obtained by a method comprising providing the two-step dental material of claim 1, mixing the components A and B at a ratio of 1:20 to 1:1 and polymerizing of the resulting polymerizable dental material.

18. The cured dental material as recited in claim 17, in the form of a core buildup material, a cement composite and/or a bulk fill composite.

19. A method for making a dental material selected from a core buildup material, a polymerizable composite cement and a bulk fill composite for producing core structures, mountings and/or tooth fillings, the method comprising providing the two-part dental material of claim 1, and including the components A and B in the dental material.

20. An add-on system (kit of parts) comprising the two-part dental material as recited in claim 1 and a dental adhesive.

21. The two-part dental material of claim 7, wherein the at least one radically polymerizable organic (meth)acrylic monomer has at least two acrylate and/or methacrylate groups.

22. The two-part dental material of claim 1, wherein the phase transfer catalyst is an ammonium salt having at least one C4 residue.

23. The two-part dental material of claim 1, wherein the phase transfer catalyst has an organic anion having 1-4 carbon atoms.

24. The two-part dental material of claim 1, wherein the phase transfer catalyst has an inorganic anion selected from hydroxides, anions of inorganic acids, pseudohalogenide anions and halogen complexes of aluminate, borate, silicate and phosphate.

* * * * *